United States Patent
Wakamatsu et al.

(10) Patent No.: US 6,946,436 B2
(45) Date of Patent: Sep. 20, 2005

(54) O/W EMULSION COMPOSITION AND METHOD OF PREPARING THE SAME

(75) Inventors: Kosaburo Wakamatsu, Kyoto (JP); Masahiko Tanaka, Otsu (JP); Noboru Yoshino, Kyoto (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 279 days.

(21) Appl. No.: 10/432,400

(22) PCT Filed: Nov. 22, 2001

(86) PCT No.: PCT/JP01/10230

§ 371 (c)(1), (2), (4) Date: May 21, 2003

(87) PCT Pub. No.: WO02/41853

PCT Pub. Date: May 30, 2002

(65) Prior Publication Data

US 2004/0029761 A1 Feb. 12, 2004

(30) Foreign Application Priority Data

Nov. 22, 2000 (JP) ........................................ 2000-355997

(51) Int. Cl.$^7$ .............................. C11D 17/00; C11D 3/37
(52) U.S. Cl. ........................ 510/417; 510/475; 424/59; 424/400; 424/401
(58) Field of Search ................................ 510/417, 475; 424/401, 59, 400

(56) References Cited

U.S. PATENT DOCUMENTS

| | | | |
|---|---|---|---|
| 4,606,913 A | * 8/1986 | Aronson et al. | ............... 424/59 |
| 5,250,290 A | 10/1993 | Giacomoni et al. | |
| 5,911,981 A | * 6/1999 | Dahms et al. | ............ 424/70.19 |
| 5,977,037 A | * 11/1999 | Giret et al. | .................. 510/122 |
| 6,316,030 B1 | * 11/2001 | Kropf et al. | ................. 424/489 |
| 6,783,766 B2 | * 11/2001 | Kropf et al. | ................. 424/401 |
| 6,716,419 B2 | * 4/2004 | Zoltowski et al. | ............. 424/64 |

FOREIGN PATENT DOCUMENTS

| | | |
|---|---|---|
| DE | 195 45 107 A1 | 6/1997 |
| EP | 0 484 199 A1 | 5/1992 |
| EP | 0 815 838 A2 | 1/1998 |
| JP | 47-26687 | 7/1972 |
| JP | 8-99860 | 4/1996 |
| JP | 9-295915 | 11/1997 |
| JP | 11-269049 | 5/1999 |
| JP | 11-276881 | 10/1999 |
| JP | 2000-256188 | 9/2000 |
| JP | 2001-199872 | 7/2001 |

* cited by examiner

Primary Examiner—Gregory E. Webb
(74) Attorney, Agent, or Firm—Finnegan, Henderson, Farabow, Garrett & Dunner, L.L.P.

(57) ABSTRACT

The present invention provides an O/W emulsion composition containing an electrolyte. More particularly, the invention provides an O/W emulsion composition excellent in emulsion stability despite its electrolyte content. The O/W emulsion composition of the invention can be prepared using an electrolyte, a polyglycerin fatty acid ester, an alkanoyl lactylic acid or the salt thereof, an acrylic acid-alkyl methacrylate copolymer, water, an oil, and preferably a polyhydric alcohol.

25 Claims, No Drawings

O/W EMULSION COMPOSITION AND METHOD OF PREPARING THE SAME

TECHNICAL FIELD

The present invention relates to an O/W emulsion composition containing an electrolyte. More particularly, the present invention relates to an O/W emulsion composition excellent in emulsion stability despite its electrolyte content. The invention further relates to a method for preparing an O/W emulsion composition excellent in emulsion stability. Moreover, the invention relates to a method for stabilizing the emulsion of an O/W emulsion composition containing an electrolyte.

BACKGROUND OF THE INVENTION

Various physiological functions of electrolytes are widely known. It is necessary, however, to incorporate at least a specific concentration of an electrolyte in order to prepare pharmaceutical compositions that are capable of effectively exhibiting the functions provided by electrolytes. Since electrolytes have a characteristic of decreasing the strength of membranes formed at oil/water interfaces, it is known that when an emulsion composition, particularly an O/W emulsion composition, containing an electrolyte is prepared, emulsion particles agglomerate and are likely to cause a separation of water and oil phases, oil floating, etc. Moreover, the emulsion itself sometimes degenerates over time due to the influence of the electrolyte, resulting changes in color and smell.

When preparing emulsion compositions containing an electrolyte, therefore, various pharmaceutical techniques are employed to improve the stability of the emulsion.

Although polyglycerin fatty acid esters are emulsifiers heretofore known to be highly safe and excellent in usability and functionality, the emulsifying ability thereof is relatively low. Therefore, when a large number of electrolytes are used, it is difficult to prepare a stable emulsion composition from the polyglycerin fatty acid ester. Recently, a nonaqueous emulsion method was proposed as a method for preparing a stable emulsion using a polyglycerin fatty acid ester (Japanese Unexamined Patent Application No. 37040/1981). Even when this method is employed, phenomena such as oil floating and the like sometimes occur as the concentration of the electrolyte increases and the emulsifying ability decreases. Further, an acrylic acid-alkyl methacrylate copolymer has recently drawn attention as an excellent high-molecular emulsifier for an O/W emulsion due to properties such as the ability to provide a stable emulsion by a small amount; the ability to be used regardless of the type of oil, thereby making it versatile; gentleness to humans and the environment; an excellent feel when applied to the skin and hair related to a lack of tackiness; etc. However, it is also reported that the viscosity and the emulsion stability are decreased when the acrylic acid-alkyl methacrylate copolymer is used with ionic components. ("Function and Application of High-Molecular Emulsifier for O/W Emulsion" *FRAGRANCE JOURNAL* 1998-8 pp. 79–83)

DISCLOSURE OF THE INVENTION

An object of the present invention is to provide an O/W emulsion composition that is excellent in emulsion stability despite having an electrolyte contained as an ingredient and that stably maintains its emulsified state over a long period of time. Another object of the invention is to provide various external preparations that exhibit, in addition to good emulsion stability, desired functions derived from the electrolyte contained as an ingredient therein, and that can be used in the field of medical or quasi-medical drugs and in the field of fragrances and cosmetics.

Still another object of the invention is to provide a method for preparing an O/W emulsion composition excellent in emulsion stability despite its electrolyte content, and a method for stabilizing the emulsion of the O/W emulsion composition containing an electrolyte.

The inventors conducted research for the purpose of stably emulsifying a composition containing an electrolyte and found that it is possible to emulsify electrolytes by the combined use of an acrylic acid-alkyl methacrylate copolymer and a known emulsifier, i.e., a polyglycerin fatty acid ester, even though the polyglycerin fatty acid ester alone could not heretofore emulsify. However, the inventors also found that the emulsion particles of the polyglycerin fatty acid ester and those of the acrylic acid-alkyl methacrylate copolymer agglomerate due to long term storage or temperature change, and they gelate on the inner wall of a container and in the upper layer of the emulsion. The inventors conducted further research in view of the above findings and discovered that the further addition of an alkanoyl lactylic acid or the salt thereof prevents the gelation caused by temperature change and disadvantages such as oil floating and separation caused by long-term storage, thus enabling an emulsion composition excellent in emulsion stability to be prepared. The present invention has been accomplished based on these findings.

Specifically, the present invention provides the O/W emulsion compositions described in the following Items 1 to 21:

Item 1. An O/W emulsion composition comprising an electrolyte, a polyglycerin fatty acid ester, an alkanoyl lactylic acid or the salt thereof, an acrylic acid-alkyl methacrylate copolymer, water, and an oil.

Item 2. An O/W emulsion composition according to Item 1, further comprising a polyhydric alcohol.

Item 3. An O/W emulsion composition according to Item 2, wherein the electrolyte is a purine nucleic acid-related substance.

Item 4. An O/W emulsion composition according to Item 3, wherein the electrolyte is at least one member selected from the group consisting of adenosine 3',5'-cyclic monophosphate, adenosine monophosphate, adenosine diphosphate, adenosine triphosphate, and the salts thereof.

Item 5. An O/W emulsion composition according to Item 3, wherein the electrolyte is adenosine monophosphate or the salt thereof.

Item 6. An O/W emulsion composition according to Item 2, wherein the polyglycerin fatty acid ester is an ester of a $C_{12-36}$ fatty acid and a polyglycerin having a polymerization degree of 6 or more.

Item 7. An O/W emulsion composition according to Item 2, wherein the polyglycerin fatty acid ester is an ester of a $C_{12-36}$ fatty acid and a polyglycerin having a polymerization degree of 6 to 10.

Item 8. An O/W emulsion composition according to Item 2, wherein the alkanoyl lactylic acid contains an alkanoyl group having 8 or more carbons.

Item 9. An O/W emulsion composition according to Item 2, wherein the alkanoyl lactylic acid contains a $C_{8-18}$ alkanoyl group.

Item 10. An O/W emulsion composition according to Item 2, wherein the acrylic acid-alkyl methacrylate copolymer contains a $C_{5-40}$ alkyl group.

Item 11. An O/W emulsion composition according to Item 2, wherein the acrylic acid-alkyl methacrylate copolymer contains a $C_{10-30}$ alkyl group.

Item 12. An O/W emulsion composition according to Item 2, wherein the oil is a hydrocarbon liquid oil.

Item 13. An O/W emulsion composition according to Item 2, wherein the electrolyte is contained in a proportion of at least 0.1 wt. % based on 100 wt. % of the emulsion composition.

Item 14. An O/W emulsion composition according to Item 2, wherein the electrolyte is contained in a proportion of 0.5 to 7 wt. % based on 100 wt. % of the emulsion composition.

Item 15. An O/W emulsion composition according to Item 2, wherein the electrolyte is contained in a proportion of 1 to 6 wt. % based on 100 wt. % of the emulsion composition.

Item 16. An O/W emulsion composition according to Item 2, wherein the polyglycerin fatty acid ester is contained in a proportion of 0.05 to 6 wt. %, the alkanoyl lactylic acid or the salt thereof is contained in a proportion of 0.01 to 1 wt. %, the acrylic acid-alkyl methacrylate copolymer is contained in a proportion of 0.01 to 0.8 wt. %, the oil is contained in a proportion of 0.3 to 20 wt. %, and the polyhydric alcohol is contained in a proportion of 0.05 to 15 wt. %, based on 100 wt. % of the emulsion composition.

Item 17. An O/W emulsion composition according to Item 2, wherein the polyglycerin fatty acid ester is contained in a proportion of 0.1 to 5.5 wt. %, the alkanoyl lactylic acid or the salt thereof is contained in a proportion of 0.1 to 0.5 wt. %, the acrylic acid-alkyl methacrylate copolymer is contained in a proportion of 0.3 to 0.6 wt. %, the oil is contained in a proportion of 0.5 to 15 wt. %, and the polyhydric alcohol is contained in a proportion of 3 to 10 wt. %, based on 100 wt. % of the emulsion composition.

Item 18. An O/W emulsion composition according to Item 2, wherein the polyglycerin fatty acid ester and the alkanoyl lactylic acid or the salt thereof are contained in a weight ratio of 95:5 to 60:40.

Item 19. An O/W emulsion composition according to Item 2, wherein the polyglycerin fatty acid ester and the alkanoyl lactylic acid or the salt thereof are contained in a weight ratio of 90:10 to 70:30.

Item 20. An O/W emulsion composition according to Item 2, further comprising a lower alcohol.

Item 21. An O/W emulsion composition according to Item 2 used for a skin cosmetic or an externally-applied medical or quasi-medical drug for the skin.

Further, the present invention provides the methods for preparing an O/W emulsion composition as defined in Items 22 to 24 below:

Item 22. A method for preparing an O/W emulsion composition comprising the steps:
1) preparing a nonaqueous emulsion using a compound comprising a polyglycerin fatty acid ester, an alkanoyl lactylic acid or the salt thereof, an oil, and, as required, a polyhydric alcohol;
2) preparing an aqueous solution using a composition comprising an electrolyte, water, and an acrylic acid-alkyl methacrylate copolymer; and
3) blending the nonaqueous emulsion with the aqueous solution to give the emulsion composition.

Item 23. A method for preparing an O/W emulsion composition according to Item 22, wherein Step 2) is for preparing the aqueous solution using the composition further comprising at least one member selected from lower alcohols and polyhydric alcohols.

Item 24. A method for preparing an O/W emulsion composition according to Item 22, wherein the method comprising incorporating the nonaqueous emulsion in a proportion of 1 to 40 wt. % based on 100 wt. % of the final emulsion composition.

The methods described above include the following embodiments:

(1) A method for preparing an O/W emulsion composition using a purine nucleic acid-related substance as an electrolyte.

(2) A method for preparing an O/W emulsion composition using, as an electrolyte, at least one member selected from the group consisting of adenosine 3',5'-cyclic monophosphate, adenosine monophosphate, adenosine diphosphate, adenosine triphosphate, and the salts thereof.

(3) A method for preparing an O/W emulsion composition using an adenosine monophosphate or the salt thereof as an electrolyte.

(4) A method for preparing an O/W emulsion composition using, as a polyglycerin fatty acid ester, an ester of a $C_{12-36}$ fatty acid and a polyglycerin having a polymerization degree of 6 or more.

(5) A method for preparing an O/W emulsion composition using, as a polyglycerin fatty acid ester, an ester of a $C_{12-36}$ fatty acid and a polyglycerin having a polymerization degree of 6 to 10.

(6) A method for preparing an O/W emulsion composition using, as an alkanoyl lactylic acid, an alkanoyl lactylic acid containing an alkanoyl group having 8 or more carbons.

(7) A method for preparing an O/W emulsion composition using, as an alkanoyl lactylic acid, an alkanoyl lactylic acid containing a $C_{8-18}$ alkanoyl group.

(8) A method for preparing an O/W emulsion composition using an acrylic acid-alkyl methacrylate copolymer containing an alkyl chain with 5 to 40 carbons as an acrylic acid-alkyl methacrylate copolymer.

(9) A method for preparing an O/W emulsion composition using an acrylic acid-alkyl methacrylate copolymer containing an alkyl chain with 10 to 30 carbons as an acrylic acid-alkyl methacrylate copolymer.

(10) A method for preparing an O/W emulsion composition using a hydrocarbon liquid oil.

(11) A method for preparing an O/W emulsion composition, wherein the method comprising incorporating an electrolyte in a proportion of at least 0.1 wt. % based on 100 wt. % of the emulsion composition.

(12) A method for preparing an O/W emulsion composition, wherein the method comprising incorporating an electrolyte in a proportion of 0.5 to 7 wt. % based on 100 wt. % of the emulsion composition.

(13) A method for preparing an O/W emulsion composition, wherein the method comprising incorporating an electrolyte in a proportion of 1 to 6 wt. % based on 100 wt. % of the emulsion composition.

(14) A method for preparing an O/W emulsion composition, wherein the method comprising incorporating a polyglycerin fatty acid ester in a proportion of 0.05 to 6 wt. %, an alkanoyl lactylic acid or the salt thereof is contained in a proportion of 0.01 to 1 wt. %, an acrylic acid-alkyl methacrylate copolymer is contained in a proportion of 0.01 to 0.8 wt. %, an oil is contained in a proportion of 0.3 to 20 wt. %, and a polyhydric alcohol is contained in a proportion of 0.05 to 15 wt. %, based on 100 wt. % of the emulsion composition.

(15) A method for preparing an O/W emulsion composition, wherein the method comprising incorporating a polyglycerin fatty acid ester in a proportion of 0.1 to 5.5 wt. %, an alkanoyl lactylic acid or the salt thereof is contained in a proportion of 0.1 to 0.5 wt. %, an acrylic acid-alkyl methacrylate copolymer is contained in a proportion of 0.3 to 0.6 wt. %, an oil is contained in a proportion of 0.5 to 15 wt. %, and a polyhydric alcohol is contained in a proportion of 3 to 10 wt. %, based on 100 wt. % of the emulsion composition.

(16) A method for preparing an O/W emulsion composition, wherein the method comprising employing a polyglycerin fatty acid ester and an alkanoyl lactylic acid or the salt thereof contained in the emulsion composition in a weight ratio of 95:5 to 60:40.

(17) A method for preparing an O/W emulsion composition, wherein the method comprising employing a polyglycerin fatty acid ester and an alkanoyl lactylic acid or the salt thereof contained in the emulsion composition in a weight ratio of 90:10 to 70:30.

(18) A method for preparing an O/W emulsion composition, wherein the O/W emulsion composition is used for a skin cosmetic or an externally-applied medical or quasi-medical drug for the skin.

Moreover, the present invention provides methods for stabilizing the emulsion of the O/W emulsion composition as defined in the following Items 25 and 27:

Item 25. A method for stabilizing the emulsion of an O/W emulsion composition containing an electrolyte, water, and an oil, the method comprising incorporating a polyglycerin fatty acid ester, an alkanoyl lactylic acid or the salt thereof, an acrylic acid-alkyl methacrylate copolymer, and, as required, a polyhydric alcohol into the emulsion composition.

Item 26. A method for stabilizing the emulsion of an O/W emulsion composition according to Item 25, wherein the method comprising incorporating the polyglycerin fatty acid ester in a proportion of 0.05 to 6 wt. %, the alkanoyl lactylic acid or the salt thereof in a proportion of 0.01 to 1 wt. %, the acrylic acid-alkyl methacrylate copolymer in a proportion of 0.01 to 0.8 wt. %, and, as required, the polyhydric alcohol in a proportion of 0.05 to 15 wt. %, based on 100 wt. % of the emulsion composition containing the oil in a proportion of 0.3 to 20 wt. %.

Item 27. A method for stabilizing the emulsion of an O/W emulsion composition, the method comprising blending a nonaqueous emulsion containing a polyglycerin fatty acid ester, an alkanoyl lactylic acid or the salt thereof, an oil, and, as required, a polyhydric alcohol with an aqueous solution containing an electrolyte, water, and an acrylic acid-alkyl methacrylate copolymer, to give the emulsion composition.

The methods described above for stabilizing the emulsion of an O/W emulsion composition include the following embodiments:

(1) A method for stabilizing the emulsion of an O/W emulsion composition, wherein the O/W emulsion composition contains a purine nucleic acid-related substance as an electrolyte.

(2) A method for stabilizing the emulsion of an O/W emulsion composition, wherein the O/W emulsion composition contains, as an electrolyte, one member selected from the group consisting of adenosine 3',5'-cyclic monophosphate, adenosine monophosphate, adenosine diphosphate, adenosine triphosphate, and the salts thereof.

(3) A method for stabilizing the emulsion of an O/W emulsion composition, wherein the O/W emulsion composition contains adenosine monophosphate or the salt thereof as an electrolyte.

(4) A method for stabilizing the emulsion of an O/W emulsion composition, wherein the O/W emulsion composition contains an electrolyte in a proportion of at least 0.1 wt. % based on 100 wt. % of the composition.

(5) A method for stabilizing the emulsion of an O/W emulsion composition, wherein the O/W emulsion composition contains an electrolyte in a proportion of 0.5 to 7 wt. % based on 100 wt. % of the composition.

(6) A method for stabilizing the emulsion of an O/W emulsion composition, wherein the O/W emulsion composition contains an electrolyte in a proportion of 1 to 6 wt. % based on 100 wt. % of the composition.

(7) A method for stabilizing the emulsion of an O/W emulsion composition, wherein the O/W emulsion composition contains a hydrocarbon liquid oil as an oil.

(8) A method for stabilizing the emulsion of an O/W emulsion composition, wherein the O/W emulsion composition contains an oil in a proportion of 0.3 to 20 wt. % based on 100 wt. % of the composition.

(9) A method for stabilizing the emulsion of an O/W emulsion composition, wherein the O/W emulsion composition contains an oil in a proportion of 0.5 to 15 wt. % based on 100 wt. % of the composition.

(10) A method for stabilizing the emulsion of an O/W emulsion composition, wherein an ester of a $C_{12-36}$ fatty acid and a polyglycerin having a polymerization degree of 6 or more is used as a polyglycerin fatty acid ester.

(11) A method for stabilizing the emulsion of an O/W emulsion composition, wherein an ester of a $C_{12-36}$ fatty acid and a polyglycerin having a polymerization degree of 6 to 10 is used as a polyglycerin fatty acid ester.

(12) A method for stabilizing the emulsion of an O/W emulsion composition, wherein an alkanoyl lactylic acid containing an alkanoyl group having 8 or more carbons is used as an alkanoyl lactylic acid.

(13) A method for stabilizing the emulsion of an O/W emulsion composition, wherein an alkanoyl lactylic acid containing a $C_{8-18}$ alkanoyl group is used as an alkanoyl lactylic acid.

(14) A method for stabilizing the emulsion of an O/W emulsion composition, wherein an acrylic acid-alkyl methacrylate copolymer containing an alkyl chain with 5 to 40 carbons is used as an acrylic acid-alkyl methacrylate copolymer.

(15) A method for stabilizing the emulsion of an O/W emulsion composition, wherein an acrylic acid-alkyl methacrylate copolymer containing a $C_{10-30}$ alkyl group is used as an acrylic acid-alkyl methacrylate copolymer.

(16) A method for stabilizing the emulsion of an O/W emulsion composition, wherein the method comprising incorporating a polyglycerin fatty acid ester in a proportion of 0.1 to 5.5 wt. %, an alkanoyl lactylic acid or the salt thereof in a proportion of 0.1 to 0.5 wt. %, an acrylic acid-alkyl methacrylate copolymer in a proportion of 0.3 to 0.6 wt. %, and, as required, a polyhydric alcohol in a proportion of 3 to 10 wt. %, based on 100 wt. % of the emulsion composition containing an oil in a proportion of 0.5 to 15 wt. %.

(17) A method for stabilizing the emulsion of an O/W emulsion composition, wherein the method comprising employing a polyglycerin fatty acid ester and an alkanoyl lactylic acid or the salt thereof contained in the emulsion composition in a weight ratio of 95:5 to 60:40.

(18) A method for stabilizing the emulsion of an O/W emulsion composition, wherein the method comprising employing a polyglycerin fatty acid ester and an alkanoyl lactylic acid or the salt thereof contained in the emulsion composition in a weight ratio of 90:10 to 70:30.

(19) A method for stabilizing the emulsion of an O/W emulsion composition, wherein the O/W emulsion composition is used for a skin cosmetic or an externally-applied medical or quasi-medical drug for the skin.

BEST MODE FOR CARRYING OUT THE INVENTION (1) O/W Emulsion Composition and Method for Preparation thereof The O/W emulsion composition of the present invention essentially contains an electrolyte, water, a polyglycerin fatty (aliphatic) acid ester, an alkanoyl lactylic acid or the salt thereof, an acrylic acid-alkyl methacrylate copolymer, and an oil.

Electrolytes usable in the invention are not limited. Preferable are those that exhibit physiological functions when applied to the skin. Examples include a wide variety of electrolytes that can be incorporated into external preparations, particularly cosmetics, and externally-applied medical and quasi-medical drugs. Preferable are those that are water soluble or hydrophilic. Specific examples of usable electrolytes are adenine, adenosine monophosphate, adenosine diphosphate, adenosine triphosphate, cyclic adenosine monophosphate, and like adenylic acid derivatives, and the salts thereof; guanine, guanosine monophosphate, guanosine diphosphate, guanosine triphosphate, and like guanylic acid derivatives, and the salts thereof; xanthine, xanthylic acid, inosinic acid, and the salts thereof, and like purine nucleic acid-related substances; uracil, cytosine, thymine, and the derivatives thereof, and like pyrimidine nucleic acid-related substances; deoxyribonucleic acid and the salt thereof, ribonucleic acid and the salt thereof, nucleoside, nucleotide, and like nucleic acid-related substances; vitamin B1, vitamin B2, vitamin B6, vitamin B12, niacin, pantothenic acid, biotin, folic acid, lipoic acid, inositol, ascorbic acid, and like water-soluble vitamins, and the derivatives thereof; serine, glycin, asparagine, aspartic acid, lysine, arginine, threonine, cysteine, glutamic acid, pyrrolidone carboxylic acid, and like amino acids, and the derivatives thereof. These electrolytes may be used alone or in combination of two or more species.

Examples of the variety of salts described above include sodium salt, potassium salt, and like alkali metal salts; arginine, lysine, and like basic amino acid salts; ammonium salt, triethanolamine salt, and the like.

Preferable electrolytes are nucleic acid-related substances, especially purine nucleic acid-related substances. Among them, adenylic acid derivatives and the salts thereof such as adenosine phosphate and the like are known to exhibit, when applied to the skin, a moisturizing effect by increasing the number of free amino acids in the horny cell layer, and, in addition, function to stimulate the turn over thereby preventing drying and aging of the skin and improving the condition of rough skin. Therefore, they are electrolytes that can be suitably used in the present invention.

Specific examples of adenosine phosphates and the salts thereof include adenosine 3',5'-cyclic monophosphate, adenosine monophosphate, adenosine monophosphate monosodium, adenosine monophosphate disodium, adenosine diphosphate, adenosine diphosphate monosodium, adenosine diphosphate disodium, adenosine triphosphate, adenosine triphosphate monosodium, adenosine triphosphate disodium, adenosine triphosphate trisodium, and the like. Preferable among these are adenosine monophosphate and the salts thereof (adenosine monophosphate monosodium and adenosine monophosphate disodium).

The proportion of the electrolyte contained in the emulsion composition is not limited insofar as each electrolyte can exhibit the desired effects. Particularly, although it varies depending on the kind of electrolyte used, it is in a range of at least 0.1 wt. %, preferably 0.5 to 7 wt. %, more preferably 1 to 6 wt. % per 100 wt. % of the final emulsion composition.

The O/W emulsion composition of the present invention contains water as an essential ingredient. Distilled water, ion-exchanged water, sterilized water, or electrolyte-containing water can be used as the water ingredient. Examples of electrolyte-containing water include sea water, hot-spring water, mineral water, and the like. The term "sea water" herein refers to surface sea water, intermediate sea water, deep sea water, and ultra deep sea water.

The proportion of the water contained in 100 wt. % of the final emulsion composition is not limited. Usually, it is suitably selected from a range of 50 to 90 wt. %. Preferably, it is selected from a range of 60 to 80 wt. %.

Polyglycerin fatty acid esters usable in the present invention are not limited. Examples include esters of a $C_{12-36}$ fatty acid and a polyglycerin having a polymerization degree of 6 or more, especially 6 to 10. Fatty acids that form esters with polyglycerins include saturated, unsaturated, linear or branched fatty acids. Specific examples are capric acid, lauric acid, isotridecanoic acid, myristic acid, palmitic acid, palmitoleic acid, stearic acid, isostearic acid, oleic acid, linoleic acid, behenic acid, ricinoleic acid, and the like.

Specific examples of polyglycerin fatty acid esters are hexaglyceryl monolaurate, hexaglyceryl monoisostearate, hexaglyceryl monomyristate, hexaglyceryl dioleate, hexaglyceryl dimyristate, hexaglyceryl dipalmitate, hexaglyceryl distearate, hexaglyceryl dibehenylate, hexaglyceryl trilaurate, hexaglyceryl trimyristate, hexaglyceryl tripalmitate, hexaglyceryl tristearate, hexaglyceryl tribehenylate, hexaglyceryl tetralaurate, hexaglyceryl tetramyristate, hexaglyceryl tetrapalmitate, hexaglyceryl tetrastearate, hexaglyceryl tetrabehenylate, hexaglyceryl pentalaurate, hexaglyceryl pentamyristate, hexaglyceryl pentapalmitate, hexaglyceryl pentastearate, hexaglyceryl pentabehenylate, decaglyceryl monocaprate, decaglyceryl monolaurate, decaglyceryl monomyristate, decaglyceryl monopalmitate, decaglyceryl monostearate, decaglyceryl monooleate, decaglyceryl monolinoleate, decaglyceryl monoisostearate, decaglyceryl dicaprate, decaglyceryl dilaurate, decaglyceryl dimyristate, decaglyceryl dipalmitate, decaglyceryl distearate, decaglyceryl diisostearate, decaglyceryl trilaurate, decaglyceryl trimyristate, decaglyceryl tripalmitate, decaglyceryl tristearate, decaglyceryl trioleate, decaglyceryl tribehenylate, decaglyceryl pentastearate, decaglyceryl pentaoleate, decaglyceryl pentaisostearate, decaglyceryl heptastearate, decaglyceryl decastearate, decaglyceryl decaoleate, decaglyceryl decaisostearate, and the like. However, the polyglycerin fatty acid esters are not limited thereto.

The polyglycerin fatty acid esters may be used alone or in combination of two or more species. Polyglycerin fatty acid esters having an HLB value of 10 or more, especially 10 to 15, can be suitably used. It is preferable to use the polyglycerin fatty acid ester in a proportion of 0.05 to 6 wt. % per 100 wt. % of the final emulsion composition, more preferably in a proportion of 0.1 to 5.5 wt. %.

Alkanoyl lactylic acids usable in the invention are not limited. Examples include alkanoyl lactylic acids having an alkanoyl group with 8 or more carbons, preferably alkanoyl lactylic acids having a $C_{8-18}$ alkanoyl group. Specific examples include octanoyl lactylic acid, caproyl lactylic acid, 2-ethyl hexanoyl lactylic acid, lauroyl lactylic acid, myristoyl lactylic acid, palmitoyl lactylic acid, stearoyl lactylic acid, isostearoyl lactylic acid, oleoyl lactylic acid, 12-hydroxystearoyl lactylic acid, linoleyl lactylic acid, and hebenoyl lactylic acid. Preferable are stearoyl lactylic acid and isostearoyl lactylic acid. The alkanoyl lactylic acids can be used in the form of a salt. Examples of such salts include sodium salts, potassium salts, and like alkali metal salts; ammonium salts, triethanolamine salts, and the like. Preferred are sodium salts, more specifically, sodium stearoyl lactylate and sodium isostearoyl lactylate.

The alkanoyl lactylic acids and the salts thereof may be used alone or in combination of two or more species. It is preferable to use the alkanoyl lactylic acid or the salt thereof in a proportion of 0.01 to 1 wt. % in 100 wt. % of the final emulsion composition, more preferably in a proportion of 0.1 to 0.5 wt. %.

The polyglycerin fatty acid esters and alkanoyl lactylic acids and the salts thereof are used as an emulsifier for the nonaqueous emulsion prepared in the production process of the emulsion composition of the invention. The proportion for blending a polyglycerin fatty acid ester with an alkanoyl lactylic acid or the salt thereof is desirably such that the HLB value of the mixture be 10 or more, preferably 10 to 13. Specific examples of the proportion for blending a polyglycerin fatty acid ester with an alkanoyl lactylic acid or the salt thereof are weight ratios of 95:5 to 60:40, preferably 90:10 to 70:30.

Acrylic acid-alkyl methacrylate copolymers usable in the invention are not limited. Examples usually include those having an alkyl chain with 5 to 40 carbons. Preferred are those having an alkyl chain with 10 to 30 carbons. Although not limited thereto, such polymers are commercially available, for example, from Goodrich Corporation under the trademarks of Carbopol and Pemulen, such as Carbopol 1342, Pemulen TR-1, and Pemulen TR-2.

The acrylic acid-alkyl methacrylate copolymers may be used alone or in combination of two or more species. It is preferable to use the acrylic acid-alkyl methacrylate copolymer in a proportion of 0.01 to 0.8 wt. % per 100 wt. % of the final emulsion composition, more preferably in a proportion of 0.3 to 0.6 wt. %, still more preferably in a proportion of 0.4 to 0.6 wt. %.

Oils usable in the invention are not limited. Specific examples include peanut oil, sesame oil, soybean oil, safflower oil, avocado oil, sunflower oil, corn oil, rapeseed oil, cottonseed oil, castor oil, camellia oil, coconut oil, olive oil, poppy oil, cacao oil, jojoba oil, and like vegetable oils; beef tallow, lard, wool oil, and like animal oils and fats; petrolatum, liquid paraffin, squalane, α-olefin oligomer, and like hydrocarbon liquid oils; isopropyl myristate, isopropyl isostearate, myristyl myristate, cetyl palmitate, cetyl isooctate, isocetyl myristate, n-butyl myristate, octyldodecyl myristate, isopropyl linolenate, propyl ricinoleate, isopropyl ricinoleate, isobutyl ricinoleate, heptyl ricinoleate, diethyl sebacate, diisopropyl adipate, and like higher fatty acid esters; white beeswax, whale wax, Japan wax, and like waxes; cetyl alcohol, stearyl alcohol, behenyl alcohol, batyl alcohol, chimyl alcohol, and like higher aliphatic alcohols; waxes; stearic acids, oleic acids, palmitic acids, and like higher fatty acids; mono-, di-, or triglyceride mixtures of $C_{12-18}$ saturated or unsaturated fatty acids; methyl polysiloxane, dimethyl polysiloxane, methylphenyl polysiloxane, methyl hydrogen polysiloxane, and like linear silicones; decamethylcyclopentasiloxane, octamethylcyclotetrasiloxane, methylcyclosiloxane, and like cyclic silicones; crosslinked methyl polysiloxane, crosslinked methylphenyl polysiloxane, and like crosslinked silicones; and, for example, silicone oils such as silicones modified by polyoxyethylene, polyoxypropylene or the like; in addition to others. Preferable are hydrocarbon liquid oils such as vaseline, liquid paraffin, squalane, α-olefin oligomer, and the like.

The oils may be used alone or in combination of two or more species. When oils are solid, it is preferable to liquefy them by means of an auxiliary resolvent before using.

It is preferable to use the oil in a proportion of 0.3 to 20 wt. % per 100 wt. % of the final emulsion composition, more preferably in a proportion of 0.5 to 15 wt. %.

Although the preparation method for the O/W emulsion composition is not limited, it is preferable to prepare it according to the method described below:
(1) The polyglycerin fatty acid ester and the alkanoyl lactylic acid or the salt thereof are mixed with the oil and preferably with the polyhydric alcohol. The mixture is stirred while being heated. After the mixture is uniformly dissolved, it is cooled to give a nonaqueous emulsion.
(2) The nonaqueous emulsion thus obtained is blended with an aqueous solution (aqueous composition) that is separately prepared and contains the electrolyte, the water, and the acrylic acid-alkyl methacrylate copolymer. The O/W emulsion composition is then prepared according to a conventional method.

It is preferable to use the polyhydric alcohol in Process (1) for preparing the nonaqueous emulsion in order to further improve the development of the emulsifying ability of the polyglycerin fatty acid ester, the alkanoyl lactylic acid, etc.

Polyhydric alcohols usable herein are not limited. Specific examples include polyglycerins having a polymerization degree of 2 to 10 (for example, diglycerin, triglycerin, tetraglycerin, etc.), ethylene glycol, diethylene glycol, polyethylene glycol, 1,3-buthylene glycol, propylene glycol, dipropylene glycol, isoprene glycol, pentadiol, sorbitol, maltitol, fructose, and the like. The use of glycerin is preferable. These polyhydric alcohols may be used alone or in combination of two or more species. In this case, the polyhydric alcohol is used in a proportion of 0.05 to 15 wt. % per 100 wt. % of the final emulsion composition, preferably in a proportion of 3 to 10 wt. %.

In Process (2), which is for emulsification, a lower alcohol can be incorporated in addition to the electrolyte, the water, and the acrylic acid-alkyl methacrylate copolymer in the aqueous solution (aqueous composition) that is blended with the nonaqueous emulsion. This enhances the percutaneous absorption of the electrolyte. Lower alcohols usable in the invention are not limited, but are usually suitably selected from alcohols having 1 to 6 carbons. Preferable examples are ethanol, propanol, isopropanol, and like $C_{1-4}$ alcohols. These lower alcohols may be used alone or in combination of two or more species. The use of ethanol is preferable. In this case, the lower alcohol is used in a proportion of 0.5 to 15 wt. % per 100 wt. % of the final emulsion composition, preferably in a proportion of 3 to 10 wt. %.

Moreover, a polyhydric alcohol can be used in the aqueous solution described above (aqueous composition). The use thereby makes it possible to control the moisturizing ability and sensory characteristics of the final emulsion composition to the desired degree. Polyhydric alcohols usable in the aqueous solution include those described above. When a polyhydric alcohol is used in the preparation of the nonaqueous emulsion, it is preferable to use polyhydric alcohols that are identical or highly compatible therewith.

Examples of the method for emulsifying the mixture of the nonaqueous emulsion and the aqueous solution (aqueous composition) include stirring the mixture under atmospheric pressure or high pressure using a homomixer. The particles of the resulting emulsion can be further refined by a homogenizer as required.

The proportion of the nonaqueous emulsion to the aqueous solution (aqueous composition) is not limited. It is usually desirable to control the proportion of the nonaqueous emulsion to 1 to 40 wt. %, preferably 1 to 30 wt. %, based on 100 wt. % of the final emulsion composition, thereby giving a more stable O/W emulsion composition.

The O/W emulsion composition of the invention, insofar as the effects of the invention are not impaired, may contain, as required, a wide range of known substances, such as humectants, UV absorbers, UV dispersants, vitamins, plant extracts, astringents, anti-inflammatory agents, whiteners, antioxidants, cell activators, and especially those known substances used in externally-applied compositions suitable for the skin, such as cosmetics and externally-applied medical/quasi-medical drugs in addition to surfactants, coloring matter (dyes, pigments), aromatics, antiseptic agents, bactericides, thickeners, antioxidants, sequestering agents, pH adjusters, deodorizers, and a wide variety of additives.

The viscosity of the O/W emulsion composition of the invention is not limited. When the O/W emulsion composition is employed as a cosmetic suitable for the skin or as an externally-applied medical or quasi-medical drug, it is usually desirable to prepare the O/W emulsion composition to have a viscosity of 30,000 cps or less, preferably 500 to 20,000 cps, at a temperature of 20° C.

The O/W emulsion composition of the invention stably maintains its emulsified state by inhibiting the oil separation that is typically caused by long-term storage under a condition in which the O/W emulsion composition is likely to be affected by temperature change, even when an electrolyte is contained therein in any amount desired in accordance with the use and the effect intended, especially in any amount desired from the range of 0.1 wt. % or more, preferably 0.1 to 6 wt. %. The O/W emulsion composition of the invention can be prepared, according to the intended use, to provide an excellent, non-tacky feel when used to the skin. The O/W emulsion composition of the invention is therefore especially useful for external preparations, such as cosmetics suitable for the skin (including the scalp), and externally-applied medical and quasi-medical drugs for the skin (including the scalp). Particularly, when adenosine monophosphate (AMP) or the salt thereof is used as an electrolyte, the invention can be prepared as a cosmetic and external preparation for the skin (medical or quasi-medical drug) that is excellent in its moisturizing effect, prevention of dryness and aging, and ability to cure rough skin due to the action of the AMP or the salt thereof.

When the O/W emulsion composition of the invention is prepared as an external preparation such as a cosmetic or an external preparation for skin (medical or quasi-medical drug), the form thereof is not limited. Examples include emulsions, suspensions, creams, and the like.

Examples of cosmetics include emollient emulsions, milky lotions, nourishing emulsions, cleansing emulsions, and like emulsions; emollient creams, massage creams, cleansing creams, makeup creams, and like creams; and the like. These cosmetics are applied to the skin in a suitable amount per application or with a suitable frequency per day, according to the age of the user, the gender, the intended use, the condition of the affected part of the skin, etc.

(2) Method for Stabilizing the Emulsion of an O/W Emulsion Composition Containing an Electrolyte The present invention also provides a method for stabilizing the emulsion of an O/W emulsion composition containing an electrolyte. This method can be demonstrated by preparing an O/W emulsion composition using an acrylic acid-alkyl methacrylate copolymer, a polyglycerin fatty acid ester, and an alkanoyl lactylic acid or the salt thereof, in addition to an electrolyte, water, and an oil, all of which are as described above. To give higher emulsion stability to the emulsion composition, a polyhydric alcohol may be further added in addition to the ingredients mentioned above.

Specifically, the method can be demonstrated by incorporating the polyglycerin fatty acid ester in a proportion of 0.05 to 6 wt. %, preferably 0.1 to 5.5 wt. %; the alkanoyl lactylic acid or the salt thereof in a proportion of 0.01 to 1 wt. %, preferably 0.1 to 0.5 wt. %; and the acrylic acid-alkyl methacrylate copolymer in a proportion of 0.01 to 0.8 wt. %, preferably 0.3 to 0.6 wt. %, more preferably 0.4 to 0.6 wt. % into 100 wt. % of the final O/W emulsion composition containing the electrolyte in a proportion of 0.1 wt. % or more, preferably 0.5 to 7 wt. %, more preferably 1 to 6 wt. %. In this case, the proportion of the oil contained in the final O/W emulsion composition is not limited, but is preferably 0.3 to 20 wt. %, more preferably 0.5 to 15 wt. %. The water accounts for the portion of the O/W emulsion composition other than that constituted by the oil and other ingredients. The proportion of the water is not limited, but is usually suitably selected from the range of 50 to 90 wt. %, preferably 60 to 80 wt. %.

It is preferable to use the polyglycerin fatty acid ester and the alkanoyl lactylic acid or the salt thereof in such a proportion that the HLB value of the mixture will be 10 or more, preferably 10 to 13. Specifically, it is preferable to use the polyglycerin fatty acid ester and the alkanoyl lactylic acid or the salt thereof in such a proportion that the weight ratio thereof will be 95:5 to 60:40, preferably 90:10 to 70:30.

When a polyhydric alcohol is incorporated, the proportion thereof is, for example, in a range of 0.05 to 15 wt. %, preferably 2 to 10 wt. %.

More specifically, the method of the invention can be demonstrated by using each ingredient in the proportion specified above and then preparing an O/W emulsion composition as described below:

1) The polyglycerin fatty acid ester and the alkanoyl lactylic acid or the salt thereof are mixed with the oil and preferably with the polyhydric alcohol. The mixture is stirred while being heated. After the mixture is uniformly dissolved, it is cooled to give a nonaqueous emulsion.

2) The nonaqueous emulsion thus obtained is blended with an aqueous solution (aqueous composition) that is separately prepared and contains the electrolyte, the water, and the acrylic acid-alkyl methacrylate copolymer. The O/W emulsion composition is then prepared according to a conventional emulsifying method.

By preparing an O/W emulsion composition as described above, emulsion stability can be given to the O/W emulsion composition, and the oil separation that is typically caused by long-term storage under conditions in which the O/W emulsion composition is likely to be affected by temperature change can be significantly inhibited, thereby providing an emulsion composition that stably maintains its emulsified state.

EXAMPLES

The present invention is described in more detail with reference to the following examples, but the scope of the present invention is not limited by these examples.

Examples 1 to 8

A polyglycerin fatty acid ester, an alkanoyl lactylate, an oil, and a polyhydric alcohol were blended, dissolved while being heated, and cooled, to prepare a uniform nonaqueous emulsion. Mixed therewith was an aqueous composition (aqueous solution) that was separately prepared by dissolving in distilled water (pure water) an electrolyte, an acrylic acid-alkyl methacrylate copolymer, a polyhydric alcohol, and a lower alcohol. The mixture was stirred by a homomixer to give the emulsion composition of the present invention (Examples 1 to 8). Table 1 shows the ingredients for the final emulsion compositions.

Each of the eight emulsion compositions thus prepared was placed in two transparent glass bottles. One bottle was left to stand for 2 weeks at a temperature of 60° C., and the other bottle was subjected to a 15-cycle test at temperatures ranging from −5° C. to 40° C. (1 cycle: 24 hours). The appearance (separation, oil floating, presence/absence of gel formation) of each emulsion composition after the test was visually observed and evaluated according to the following criteria.

<Evaluation Criteria>

○: Neither separation, oil floating, nor gel formation was observed.

X: Separation, oil floating, or gel formation was observed.

For comparison, an emulsion composition (Comparative Example 1) containing no alkanoyl lactylate, and an emulsion composition (Comparative Example 2) containing no acrylic acid-alkyl methacrylate copolymer were prepared in the same manner as in Examples 1 to 8 (Table 2 shows the ingredients for these emulsion compositions), and were subjected to the emulsion stability test as described above.

Tables 1 and 2 show the results of the emulsion stability test for the emulsion compositions of Examples 1 to 8 and Comparative Examples 1 to 2.

TABLE 1

| | | Ex. 1 | Ex. 2 | Ex.3 | Ex. 4 | Ex. 5 | Ex. 6 | Ex. 7 | Ex. 8 |
|---|---|---|---|---|---|---|---|---|---|
| 1 | Decaglyceryl monoisostearate | — | 1.6 | 0.16 | 4.8 | — | 4.8 | — | 1.6 |
| 2 | Decaglyceryl diisostearate | 1.2 | — | — | — | 1.2 | — | 1.2 | — |
| 3 | Decaglyceryl monostearate | — | — | 0.02 | 0.5 | — | 0.5 | — | 0.2 |
| 4 | Decaglyceryl monomyristate | 0.6 | 0.2 | — | — | 0.6 | — | 0.6 | — |
| 5 | Sodium stearoyl lactate | — | — | 0.02 | — | — | — | — | 0.2 |
| 6 | Sodium isostearoyl lactate | 0.2 | 0.2 | — | 0.5 | 0.2 | 0.5 | 0.2 | — |
| 7 | Squalane | 5.0 | 8.0 | — | 15.0 | 3.0 | 15.0 | — | 5.0 |
| 8 | α-Olefin oligomer | — | — | 5.0 | — | 2.0 | — | 5.0 | — |
| 9 | Purified glycerin | 6.0 | 6.0 | 2.0 | 9.0 | 4.0 | 10.0 | 8.0 | 9.0 |
| 10 | Dipropylene glycol | — | — | 5.0 | — | 2.0 | — | — | — |
| 11 | Adenosine monophosphate disodium | 1.5 | 1.5 | 3.0 | 6.0 | — | — | — | — |
| 12 | Sodium L-ascorbic acid phosphate ester | — | — | — | — | 2.0 | 3.0 | — | — |
| 13 | Sodium DL-pyrrolidonecarboxylate solution | — | — | — | — | — | — | 2.0 | 3.0 |
| 14 | Acrylic acid-alkyl methacrylate copolymer | 0.4 | 0.5 | 0.5 | 0.5 | 0.5 | 0.5 | 0.4 | 0.5 |
| 15 | Ethanol | 5.0 | 5.0 | 3.0 | 5.0 | 6.0 | 3.0 | 5.0 | 3.0 |
| 16 | pH Adjuster | * | * | * | * | * | * | * | * |
| 17 | Antiseptic agent | * | * | * | * | * | * | * | * |
| 18 | Pure water | Remainder | Remainder | Remainder | Remainder | Remainder | Remainder | Remainder | Remainder |
| | Viscosity (cps) 20° C. | 4,200 | 17,000 | 1,400 | 1,100 | 3,600 | 900 | 1,800 | 3,300 |
| | Long-term stability (60° C.: 2 weeks) | ○ | ○ | ○ | ○ | ○ | ○ | ○ | ○ |
| | Long-term stability (−5 to 40° C. cycles: 2 weeks) | ○ | ○ | ○ | ○ | ○ | ○ | ○ | ○ |

*: Appropriate quantity

TABLE 2

| | | Comp Ex. 1 | Comp Ex. 2 |
|---|---|---|---|
| 1 | Tetraglyceryl monoisostearate | — | — |
| 2 | Decaglyceryl monoisostearate | 2.0 | — |
| 3 | Decaglyceryl diisostearate | — | 1.2 |
| 4 | Decaglyceryl monostearate | — | — |
| 5 | Decaglyceryl monomyristate | — | 0.6 |
| 6 | Sodium stearoyl lactate | — | — |
| 7 | Sodium isostearoyl lactate | — | 0.2 |
| 8 | Squalane | 5.0 | — |
| 9 | α-Olefin oligomer | — | 5.0 |
| 10 | Purified glycerin | 6.0 | 8.0 |
| 11 | Carboxyvinyl polymer | — | 0.6 |
| 12 | Adenosine monophosphate disodium | 3.0 | 3.0 |
| 13 | Sodium L-ascorbic acid phosphate ester | — | — |
| 14 | Sodium DL-pyrrolidonecarboxylate solution | — | — |
| 15 | Acrylic acid-alkyl methacrylate copolymer | 0.5 | — |
| 16 | Ethanol | 3.0 | 5.0 |
| 17 | pH Adjuster | Appropriate quantity | Appropriate quantity |
| 18 | Antiseptic agent | Appropriate quantity | Appropriate quantity |
| 19 | Pure water | Remainder | Remainder |
| | Viscosity (cps) 20° C. | 2,000 | 1,200 |
| | Long-term stability (60° C.: 2 weeks) | ○ | x |

TABLE 2-continued

|  | Comp Ex. 1 | Comp Ex. 2 |
|---|---|---|
| Long-term stability (−5 to 40° C. cycles: 2 weeks) | x | ○ |

As can be seen from the tables, the O/W emulsion composition of the present invention inhibits water/oil phase separation, oil floating and gel formation and stably maintains its emulsified state under conditions in which the emulsion composition is likely to be affected by long-term storage and temperature change, even when it contains a relatively large amount of electrolyte as in the emulsion composition of Example 4. On the other hand, as the comparative examples show, the emulsion composition containing no acrylic acid-alkyl methacrylate copolymer (Comparative Example 2) lacked long-term emulsion stability, and the emulsion composition containing no alkanoyl lactylate (Comparative Example 1) gelated due to the temperature change, thus failing to maintain a stable emulsified state.

Administration Examples 1 to 7
Milky Lotions

O/W emulsion compositions having the formulation of Examples 1 and 3 to 8 (in Table 1) were prepared as milky lotions (Administration Examples 1 to 7) in the same manner as the Examples.

| Administration Example 8 Lotion | |
|---|---|
| Sodium DL-pyrrolidonecarboxylate solution | 1.0 Wt. % |
| Decaglyceryl monoisostearate | 0.16 |
| Decaglyceryl monostearate | 0.02 |
| Sodium stearoyl lactate | 0.02 |
| α-Olefin oligomer | 0.5 |
| Purified glycerin | 2.0 |
| Dipropylene glycol | 5.0 |
| Acrylic acid-alkyl methacrylate copolymer | 0.5 |
| Ethanol | 3.0 |
| pH adjuster | Suitable quantity |
| Antiseptic agent | Suitable quantity |
| Pure water | Remainder |
| Total | 100.00 Wt. % |

Decaglyceryl monoisostearate, decaglyceryl monostearate, sodium stearoyl lactate, α-olefin oligomer, purified glycerin, and dipropylene glycol were blended, dissolved while being heated, and cooled, to prepare a uniform nonaqueous emulsion. Mixed therewith is a separately-prepared aqueous composition containing a sodium DL-pyrrolidonecarboxylate solution, an acrylic acid-alkyl methacrylate copolymer, and ethanol. The mixture is stirred to give a lotion.

INDUSTRIAL APPLICABILITY

The present invention provides an O/W emulsion composition excellent in long-term emulsion stability despite its electrolyte content, which is generally considered to make emulsification difficult. The invention also provides a method for increasing the emulsion stability of an O/W emulsion composition containing a comparatively large amount of electrolyte. The present invention, therefore, provides an electrolyte-containing O/W emulsion composition that can efficiently exhibit the various physiological functions of the electrolyte.

The O/W emulsion composition of the invention can contain a large amount of electrolyte in a stable manner and is thus useful for cosmetics and external preparations (medical and quasi-medical drugs) for the skin containing electrolytes as active ingredients. Especially, O/W emulsion compositions containing adenosine monophosphate (AMP), the salt thereof, or like nucleic acid-related substances can effectively exhibit the moisturizing and skin exfoliation-promoting action of these substances, and are therefore useful for cosmetics and external preparations for skin that are effective in preventing fine wrinkles, giving elasticity to the skin, and providing other like effects to keep the skin from aging and to beautify the skin.

Further, the present invention provides an O/W emulsion composition that has, in addition to excellent long-term emulsion stability, an excellent feel when used on the skin, with significantly suppressed oiliness and tackiness, which is achieved by appropriately controlling the types and proportions of the electrolyte, polyglycerin fatty acid ester, alkanoyl lactylic acid or the salt thereof, acrylic acid-alkyl methacrylate copolymer, polyhydric alcohol, water, and oil contained therein.

As described above, the O/W emulsion composition of the invention is useful especially for externally-applied agents, for example, skin cosmetics (including cosmetics for the scalp) and externally-applied medicines and quasi-medicines for the skin (including the scalp).

What is claimed is:

1. An O/W emulsion composition comprising a purine nucleic acid-related substance, a polyglycerin fatty acid ester, an alkanoyl lactylic acid or the salt thereof, an acrylic acid-alkyl methacrylate copolymer, water, and an oil.

2. An O/W emulsion composition according to claim 1, further comprising a polyhydric alcohol.

3. An O/W emulsion composition according to claim 1, wherein the purine nucleic acid-related substance is at least one member selected from the group consisting of adenosine 3',5'-cyclic monophosphate, adenosine monophosphate, adenosine diphosphate, adenosine triphosphate, and the salts thereof.

4. An O/W emulsion composition according to claim 2, wherein the purine nucleic acid-related substance is adenosine monophosphate or the salt thereof.

5. An O/W emulsion composition according to claim 2, wherein the polyglycerin fatty acid ester is an ester of a $C_{12-36}$ fatty acid and a polyglycerin having a polymerization degree of 6 or more.

6. An O/W emulsion composition according to claim 2, wherein the polyglycerin fatty acid ester is an ester of a $C_{12-36}$ fatty acid and a polyglycerin having a polymerization degree of 6 to 10.

7. An O/W emulsion composition according to claim 2, wherein the alkanoyl lactylic acid contains an alkanoyl group having 8 or more carbons.

8. An O/W emulsion composition according to claim 2, wherein the alkanoyl lactylic acid contains a $C_{8-18}$ alkanoyl group.

9. An O/W emulsion composition according to claim 2, wherein the acrylic acid-alkyl methacrylate copolymer contains a $C_{5-40}$ alkyl group.

10. An O/W emulsion composition according to claim 2, wherein the acrylic acid-alkyl methacrylate copolymer contains a $C_{10-30}$ alkyl group.

11. An O/W emulsion composition according to claim 2, wherein the oil is a hydrocarbon liquid oil.

12. An O/W emulsion composition according to claim 2, wherein the purine nucleic acid-related substance is contained in a proportion of at least 0.1 wt. % based on 100 wt. % of the emulsion composition.

13. An O/W emulsion composition according to claim 2, wherein the purine nucleic acid-related substance is contained in a proportion of 0.5 to 7 wt. % based on 100 wt. % of the emulsion composition.

14. An O/W emulsion composition according to claim 2, wherein the purine nucleic acid-related substance is contained in a proportion of 1 to 6 wt. % based on 100 wt. % of the emulsion composition.

15. An O/W emulsion composition according to claim 2, wherein the polyglycerin fatty acid ester is contained in a proportion of 0.05 to 6 wt. %, the alkanoyl lactylic acid or the salt thereof is contained in a proportion of 0.01 to 1 wt. %, the acrylic acid-alkyl methacrylate copolymer is contained in a proportion of 0.01 to 0.8 wt. %, the oil is contained in a proportion of 0.3 to 20 wt. %, and the polyhydric alcohol is contained in a proportion of 0.05 to 15 wt. %, based on 100 wt. % of the emulsion composition.

16. An O/W emulsion composition according to claim 2, wherein the polyglycerin fatty acid ester and the alkanoyl lactylic acid or the salt thereof are contained in a weight ratio of 95:5 to 60:40.

17. An O/W emulsion composition according to claim 2, the polyglycerin fatty acid ester and the alkanoyl lactylic acid or the salt thereof are contained in a weight ratio of 90:10 to 70:30.

18. An O/W emulsion composition according to claim 2, further comprising a lower alcohol.

19. An O/W emulsion composition according to claim 2 used for a skin cosmetic or an externally-applied medical or quasi-medical drug for the skin.

20. A method for preparing an O/W emulsion composition comprising the steps:
1) preparing a nonaqueous emulsion using a composition comprising a polyglycerin fatty acid ester, an alkanoyl lactylic acid or salt thereof, an oil, and, as required, a polyhydric alcohol;
2) preparing an aqueous solution using a composition comprising a purine nucleic acid-related substance, water, and an acrylic acid-alkyl methacrylate copolymer; and
3) bending the nonaqueous emulsion with the aqueous solution to give the emulsion composition.

21. A method for preparing an O/W emulsion composition according to claim 20, wherein Step 2) is for preparing the aqueous solution using the composition further comprising at least one member selected from lower alcohols and polyhydric alcohols.

22. A method for preparing an O/W emulsion composition according to claim 20, wherein the method comprising incorporating the nonaqueous emulsion in a proportion of 1 to 40 wt. % based on 100 wt. % of the final emulsion composition.

23. A method for stabilizing the emulsion of an O/W emulsion composition containing a purine nucleic acid-related substance, water, and an oil, the method comprising incorporating a polyglycerin fatty acid ester, an alkanoyl lactylic acid or the salt thereof, an acrylic acid-alkyl methacrylate copolymer, and, as required, a polyhydric alcohol into the emulsion composition.

24. A method for stabilizing the emulsion of an O/W emulsion composition according to claim 23, wherein the method comprising incorporating the polyglycerin fatty acid ester in a proportion of 0.05 to 6 wt. %, the alkanoyl lactylic acid or the salt thereof in a proportion of 0.01 to 1 wt. %, the acrylic acid-alkyl methacrylate copolymer in a proportion of 0.01 to 0.8 wt. %, and, as required, the polyhydric alcohol in a proportion of 0.05 to 15 wt. % based on 100 wt. % of the emulsion composition containing the oil in a proportion of 0.3 to 20 wt. %.

25. A method for stabilizing the emulsion of an O/W emulsion composition, the method comprising blending a nonaqueous emulsion containing a polyglycerin fatty acid ester, an alkanoyl lactylic acid or the salt thereof, an oil, and, as required, a polyhydric alcohol with an aqueous solution containing a purine nucleic acid-related substance, water, and an acrylic acid-alkyl methacrylate copolymer, to give the emulsion composition.

* * * * *